United States Patent [19]

Perry

[11] 4,096,632
[45] Jun. 27, 1978

[54] DENTURE MATCHING APPARATUS

[76] Inventor: William V. Perry, 3300 Mannion Rd., Saginaw, Mich. 48603

[21] Appl. No.: 689,637

[22] Filed: May 24, 1976

[51] Int. Cl.$^2$ .............................................. A61C 11/00
[52] U.S. Cl. ...................................................... 32/32
[58] Field of Search ......................................... 32/32

[56] References Cited

U.S. PATENT DOCUMENTS

| 1,841,728 | 1/1932 | Halvorsen | 32/32 |
| 2,608,762 | 9/1952 | Fox | 32/32 |

*Primary Examiner*—Robert Peshock

[57] ABSTRACT

A dental articulator for precisely aligning and orienting dentures comprising a frame, a pair of longitudinally spaced denture mounts for releasably mounting dentures in opposing relation, mechanism mounting each of said denture mounts on the frame for universal movement as well as for bodily movement toward and away from each other to permit the dentures to be precisely aligned and oriented relative to each other, and clamp members for clamping the mount members in any of a plurality of adjusted, oriented positions while permitting limited swinging movement of at least one of the mount members on the frame.

20 Claims, 3 Drawing Figures

DENTURE MATCHING APPARATUS

BACKGROUND OF THE INVENTION

This invention relates to a dental articulator and more particularly to new and novel denture clamps and new and novel mechanism for mounting the denture clamps for relative movement so that the dentures can be precisely aligned.

The proper formation of artificial dentures requires the proper correlation and spacing of teeth in the upper denture relative to the teeth in the lower denture. It sometimes occurs that, when the dentures are initially formed, one of the teeth in the lower denture, for example, will protrude to form a "high spot" and set up localized contact stresses and interference with an abutting tooth in the upper denture.

Articulators have been provided heretofore which stationarily mount one of the dentures in a casting and adjustably or articulately mount the other denture on the frame for movement to dispose the upper denture in opposing relation with the lower denture. A sheet of carbon paper is placed between the teeth and as the teeth are brought together, those teeth having "high spots" will be appropriately marked with the carbon paper. When the user separates the teeth, he can then grind or otherwise relieve the interferring tooth portions. In the prior art device, substantial energy, money and materials is required to form the casting material and the denture forming process is delayed while the casting material, which mounts the one denture, sets. Since only one of the denture mounts is articulately movable in the prior art device, the manipulation and the adjustments heretofore have required a high degree of skill and considerable experience.

Accordingly, it is an object of the present invention to provide apparatus which will precisely align opposing dentures.

It is another object of the present invention to provide denture mounting apparatus which articulately mounts each of the dentures.

It is a further object of the present invention to provide denture mounting apparatus which will selectively permit movement of each of the dentures in any plane relative to the other denture so that the dentures can be precisely aligned.

Yet another object of the present invention is to provide denture mounting apparatus which permits each of the denture mounting clamps to bodily move relative to the other denture mounting clamps.

It is still another object of the present invention to provide a dental articulator including denture mounts which can be oriented in any plane to align the dentures, clamp members for clamping the dentures in the adjusted aligned position, and apparatus permitting swinging movement of the dentures after being clamped in the adjusted position so that carbon paper or the like can be disposed between the dentures.

Still another object of the present invention is to minimize the time required to process dentures.

Another object of the present invention is to provide a new and novel dental articulator including new and novel universal mounting joints and clamps for clamping the joints in any of a plurality of adjusted positions.

Still another object of the present invention is to provide new and novel denture mounts which can securely but releasably grip a denture.

It is another object of the present invention to provide a denture mount of the type described having relatively movable clamp members which will clamp opposite surfaces of a denture to releasably grip the denture.

Other objects and advantages of the present invention will become apparent to those of ordinary skill in the art as the description thereof proceeds.

SUMMARY OF THE INVENTION

A dental articulator comprising first and second longitudinally spaced denture gripping members for releasably gripping a pair of dentures; adjustable coupling means coupling the denture gripping members together to permit, in one position of adjustment, bodily movement of the denture gripping members toward and away from each other and to permit relative swinging movement of each denture gripping member in any plane relative to the other denture gripping member such that the dentures mounted on the denture gripping members may be moved between remote positions to abutting positions in which the dentures are precisely oriented and aligned as they would be oriented and aligned in a persons mouth, and mechanism for slectively clamping the adjustable coupling mechanism to the denture gripping members to inhibit movement of the denture gripping members and secure the dentures in the abutting positions. dr The present invention may more readily be understood by reference to the accompanying drawings in which:

DESCRIPTION OF THE PREFERRED EMBODIMENT

Figure 2:
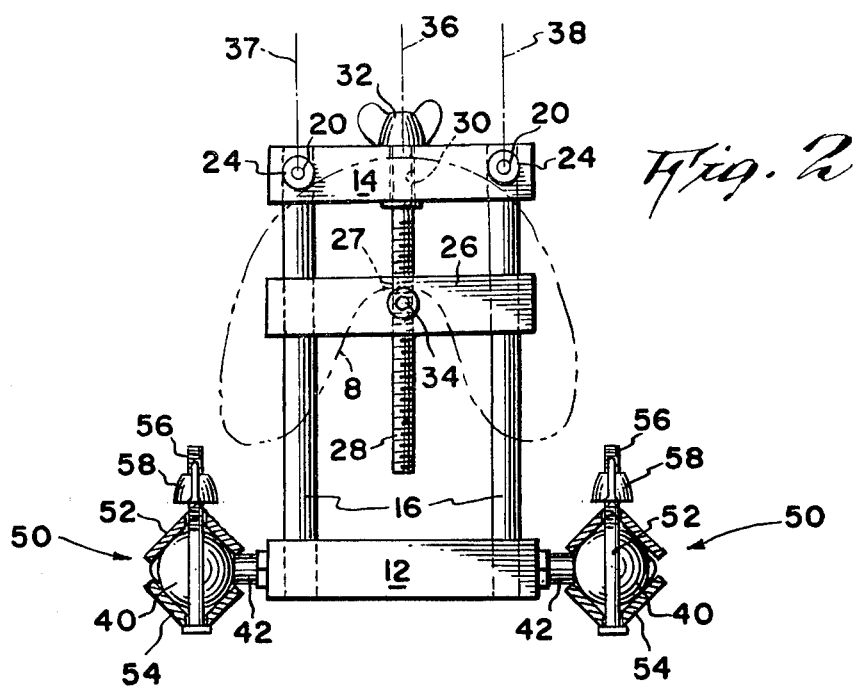
FIG. 2 is a sectional end view taken along the line 2—2 of FIG. 1.
Figure 3:
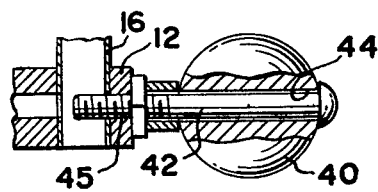
FIG. 3 is an enlarged sectional view taken along the line 3—3 of FIG. 1 illustrating one of the denture gripping mount members.

Apparatus constructed according to the present invention is particularly adapted for use in matching or aligning an upper denture, generally designated 4, and a lower denture, generally designated 5. The lower denture 5 includes a base plate 6 mounting a plurality of teeth 7. The upper denture 4 includes a base 6a mounting a plurality of teeth 7a. The lower base plate 6a differs from the upper base plate 6 in that it includes a central recess 8 along the rear side thereof (FIG. 2), as usual.

Apparatus constructed according to the present invention comprises a set of identical, upstanding, opposed denture gripping or denture clamping members, generally designated 10. Each of the denture clamp members 10 includes a pair of vertically spaced, laterally extending cross bars 12 and 14 spanning a pair of upstanding guide bars 16. The upper lateral cross bar 14, threadedly mounts via lock nuts 22, a pair of laterally spaced apart denture gripping projections or pins 20.

A slide, generally designated 26, is slidably mounted on the guide rods 16 and includes a central, threaded aperture 27 which threadedly receives a screw 28 that is freely received in a central aperture 30 provided in the upper cross bar 14. A manually graspable bolt head 32 is fixed to the upper end of the screw 28 for turning the screw 28 about its axis.

The slides 26 each mounts via nuts 22a, a denture gripping projection or pin 34 which bears against the inside edge of the respective bases 6 or 6a. The projection 34 on the slide for the lower base plate is received in the denture recess 8 for gripping the inside surface of the denture bases 6 and 6a. The denture gripping pins 20 and 34 may be suitably coated with a covering 24 which will not marr the base plates 6 and 6a of the dentures 4 and 5.

As is readily apparent, the screws 32 can be adjusted to selectively clamp and unclamp the denture bases 6 and 6a between the upper laterally spaced pins 20 and the lower pin 34. The lower pin 34 lies in a vertical plane 36 which is between vertical planes 37 and 38 intersecting the axes of the denture gripping pins 22. As will become more readily apparent hereinafter, the mounting of the dentures 4 and 5 on the denture mounting members 10 need not be precise. The dentures 4 and 5 can be initially canted or disoriented relative to each other. It is generally advisable, however, that the dentures 4 and 5 be initially mounted in the positions illustrated in FIGS. 1 and 2.

The lower, laterally extending cross bars 12 are each mounted on a pair of universal joints comprising spherical balls 40 via pins 42 snuggly received with a slip or interference fit in an opening 44 provided in the balls 40. The inner ends of the pins 42 are threaded into the transverse bars 12 as illustrated at 45. Locknuts 46 (FIG. 2) releasably lock the pins 42 to the mounting blocks 44. A spacer washer 48 is freely received on the pin 42 between the nut 46 and the inside of the ball 40.

Figure 1:
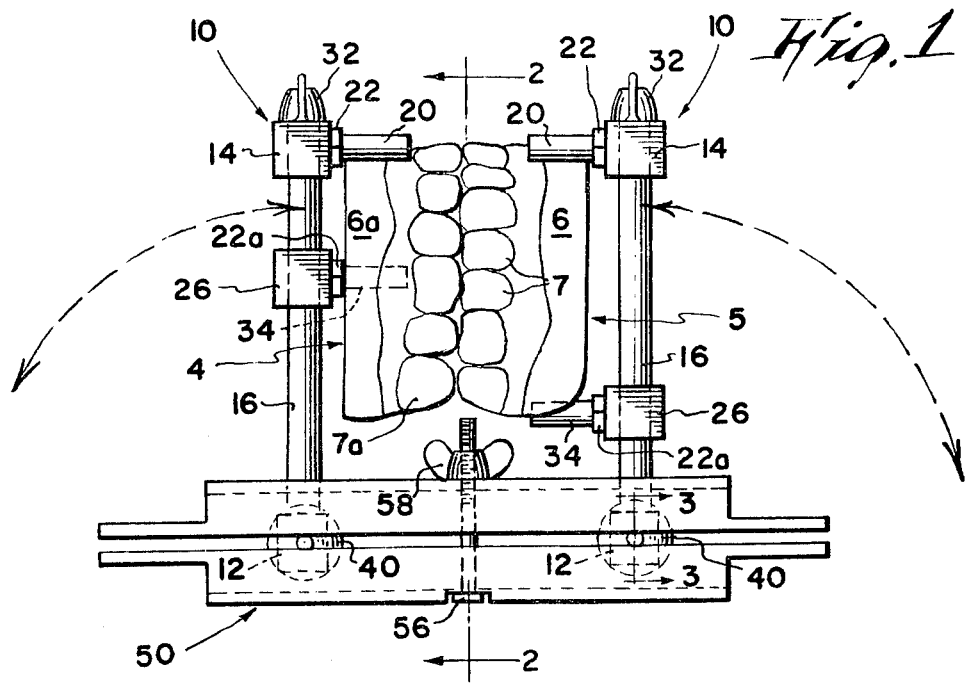
FIG. 1 is a side elevational view of apparatus constructed according to the present invention.

Apparatus for selectively clamping the denture mounts 10 in any of a plurality of adjusted positions, such as that in which the dentures are aligned illustrated in FIG. 1, the clamping apparatus comprises a frame including first and second sets of clamps, generally designated 50. Each of the clamps 50 comprise upper and lower, longitudinally extending, opposed V-shaped clamps which span the spherical mounting balls 40 on the opposed clamps 50. The clamp bars 52 and 54 are vertically movable between removed positions in which the balls 40 are free to move in any plane and clamping positions, illustrated in FIG. 2, via clamping screws 56 received in the upper and lower bars 52,54 and clamping nuts 58 disposed on the upper side of the upper bar 52. When the nuts 58 are turned on the screws 56 the bars 52 and 54 will be forced into intimate engagement with the spherical mounting members 40 to hold the spherical mounting members 40 in the adjusted positions. The bars 52 and 54 engage the spherical mounting members with point contact.

The horizontal mounting pins 42 are snugly received in the balls 40 with such a fit that the balls 40 will move with the pins 42 when the clamp bars 52 and 54 are in the unclamped position but will permit the pins 42 and denture mounts 50 and bars 12 to swing about the axis of the pins 42 when the clamp bars 54 and 52 are in the clamping position. When the clamping bars 52 and 54 are in the removed or inoperative positions, the entire mount 10 may be bodily moved toward and away from the other mount 10 and can be concurrently moved in any plane relative to the other mount 10 such that the dentures 4 and 5 may be moved into positions in which they are precisely oriented and aligned as they would be oriented and aligned in a persons mouth.

The clamp bars 52 and 54, when clamped, will prevent all movement of the mounts 10 except about the axes of the pivot pins 42. This new and novel mount eliminates play and thus the dentures may be more accurately formed.

THE OPERATION

The lower frame or clamping bars 54 are initially supported on the horizontal surface such as a table or the like. The wing nuts 58 are unturned to release the clamps 52 and 54 and the mounts 10 are swung downwardly to the horizontal positions supported on the table. The mounts 10 are swung apart and the screws 28 are turned about their axes to vertically move the slides 26 downwardly a sufficient distance as to receive the bases 6 and 6a. The screws 28 are then turned in the opposite direction to clamp the bases 6 and 6a between the denture gripping projections 34 and 20.

After the dentures 4 and 5 are releasably clamped on the mounts 10, the operator grasps the mount 10 in his hands and adjusts them relative to each other in any plane while bodily moving the spherical joints 40 toward and away from each other as necessary and appropriate between the unclamped bars 52 and 54. The denture teeth 7 and 7a may be quickly and immediately oriented and adjusted to precisely match the dentures in the positions in which they would be in a persons mouth. When the dentures are aligned, the operator can hold the dentures in the asjusted position with one hand while turning the nuts 58 with the other hand to clamp the clamping bars 52 and 54 tightly against the spherical balls 40.

When the clamping screws 56 are in their clamping positions, the clamp bars 52 and 54 on opposite sides of the frame may well be oppositely inclined and not lying in the same plane. Accordingly, the denture plates 4 and 5 may be initially mounted on the pins 20 and 34 in a variety of relative positions and yet by manipulating the relative positions of the balls 40 between the clamps bars 52 and 54, the teeth may quickly be brought into alignment. The bars 52 and 54 permit relative vertical movement, to and fro movement and sidewise movement of the mounts 10 to permit the user to quickly align the dentures.

Once the dentures are aligned in abutting relation and the clamp bars 52 and 54 tightly grip the spherical balls 40, the operator will then swing only one of the denture plates 4 and 5 about the axis of the appropriate pin 42 to a removed position so that carbon paper (not shown) can be inserted between the teeth. The teeth which are then returned to the closed position. If the free space clearance between the dentures is not proper, any high spots on the dentures will occlude the paper and be marked with the carbon on the carbon paper. The operator then will swing the denture plate 4 or 5 about the axes 42 to a horizontal position, remove the carbon paper, and then relieve the "raised" portion marked with the carbon. As soon as the raised portion is filed, the operator will replace the carbon paper and return the denture plate to the position illustrated in FIG. 1 about the axis 42 and the properly aligned position of the denture plates 4 and 5 will immediately reestablish without any further manipulation on the part of the user.

One of the dentures is again swung to a removed position. If any "high spots" are identified, they are relieved as previously described. The operation will be repeated until all "high spots" are removed. The dentures 4 and 5 are thereafter quickly removed from the denture gripping clamp pins by turning the screw 32 in an appropriate direction.

It is to be understood that the drawings and descriptive matter are in all cases to be interpreted as merely illustrative of the principles of the invention, rather than as limiting the same in any way, since it is contemplated that various changes may be made in various elements to achieve like results without departing from the spirit of the invention or the scope of the appended claims.

What I claim is:

1. Denture mounting apparatus comprising:
   first and second, longitudinally spaced, denture support members for supporting a pair of dentures;
   adjustable coupling means for coupling one support member to the other support member;
   said coupling means, in one position of adjustment, permitting relative bodily movement of said support members, toward and away from each other and for concurrent relative swinging movement of said support members in any plane relative to each other such that said dentures mounted on said support member may be moved between remote positions and abutting positions in which the dentures are precisely oriented and aligned as they should be oriented and aligned in a persons mouth;
   said coupling means being adjustable to a clamping position of adjustment in which said dentures are aligned and abutting and in which said bodily movement is prevented and said swinging movement is restricted; and
   means for selectively clamping said adjustable means to said support members in said clamping position of adjustment to inhibit movement of said support members and releasably secure said dentures in said abutting positions;
   each of said support members being mounted on a pair of laterally spaced swivel balls for movement therewith when said adjustable means is in said one position of adjustment and for swinging movement relative thereto when said adjustable means is in said clamping position; said adjustable coupling means being coupled to said swivel balls.

2. The apparatus as set forth in claim 1 wherein said support member includes an axle frictionally received by said swivel balls.

3. The apparatus as set forth in claim 1 wherein said denture support members each comprise a pair of guide rods, first and second opposed denture clamps mounted on said guide rods for to-and-fro movement relative to each other between removed positions and denture gripping positions, and means for holding said denture gripping means in said denture gripping positions.

4. The apparatus as set forth in claim 3 wherein said first denture gripping means comprises a pair of laterally spaced denture gripping projections and said second denture gripping means comprises a denture gripping projection lying in a plane between two parallel planes intersecting said pair of laterally spaced denture gripping projections.

5. Denture mounting apparatus comprising:
   first and second longitudinally spaced denture support members for supporting a pair of dentures;
   first and second laterally spaced swivel mounting balls on each of said denture support members.
   adjustable means adjustably coupling the swivel mounting balls on one support member to the swivel mounting balls on the other support member to permit, in one position of adjustment, relative bodily movement the swivel balls on one support member toward and away from the swivel balls on the other support member, and concurrent relative movement of said one support means in any plane relative to the other support means such that the dentures can be moved from removed positions to a butting aligned positions;
   means for selectively clamping said adjustable means to said swivel balls when said balls are in any selected one of a plurality of adjusted positions to prevent relative movement of said swivel mounting balls; and
   means permitting relative swinging movement of at least one of said support members relative to said swivel balls when said balls are clamped to permit selective swinging movement of one of said dentures between said abutting position and a removed position.

6. The apparatus as set forth in claim 5 wherein each of said denture support members comprises first and second denture gripping means for releasably gripping a denture; means mounting said first and second denture gripping means for relative movement toward and away from each other between spaced, inoperative positions and less spaced, denture gripping positions; and means for relatively moving said denture gripping means between said removed positions and said denture gripping positions.

7. The apparatus as set forth in claim 5 wherein each of said adjustable coupling means comprises elongate bars having V-shaped, end cross-sections, one of said elongate bars being inverted relative to the other bar and disposed in confronting relation on vertically opposite sides of said swivel balls.

8. Denture mounting apparatus comprising:
   first and second, longitudinally spaced, denture support members for supporing a pair of dentures;
   adjustable coupling means for coupling one support member to the other support member;
   said coupling means, in one position of adjustment, permitting relative bodily movement of said support members, toward and away from each other and for concurrent relative swinging movement of said support members in any plane relative to each other such that said dentures mounted on said support member may be moved between remote positions and abutting positions in which the dentures are precisely oriented and aligned as they should be oriented and aligned in a persons mouth;
   said coupling means being adjustable to a clamping position of adjustment in which said dentures are aligned and abutting and in which said bodily movement is prevented and said swinging movement is restricted; and
   means for selectively clamping said adjustable means to said support members in said position of adjustment to inhibit movement of said support members and releasably secure said dentures in said abutting positions;
   said denture support members being generally upstanding when said dentures are in said abutting positions;
   each support member including laterally spaced apart swivel mounting portions;
   said adjustable coupling means including laterally spaced pairs of longitudinally extending, vertically spaced, vertically adjustable coupling members spanning the swivel mounting portions on said denture support members;
   said clamping means including vertically adjustable means for vertically moving said vertically adjustable coupling members into clamping engagement with said swivel mounting portions.

9. Denture mounting apparatus comprising:
first and second clamp means for releasably gripping opposite sides of a denture;
means mounting said first and second clamp means for relative movement toward and away from each other between spaced, non-gripping positions and less spaced, denture gripping positions; and
means for relatively moving said first and second clamp means between said removed positions and said denture gripping positions;
said mount means comprising a pair of laterally spaced spherical bearing means and means for individually clamping said bearing means in said non-gripping positions and said gripping positions.

10. The apparatus set forth in claim 1 wherein said means for moving comprises a threaded screw.

11. The apparatus as set forth in claim 1 wherein said means mounting said clamp means comprises a guide member and slide mechanism slidably mounted thereon for movement in a longitudinal path, said slide member mounting one of said clamp means, the other of said clamp means being stationarily mounted on said guide member.

12. The apparatus as set forth in claim 11 wherein said first and second clamp means comprises denture clamping projections projecting transversely to said longitudinal path.

13. The apparatus as set forth in claim 12 wherein one of said first and second clamp means comprises a pair of laterally spaced, transversely extending denture gripping projections for bearing against the exterior surface of a denture and the other clamp means comprises a denture gripping projection lying in a plane disposed between said pair of projections for bearing against the inner surface of a denture.

14. The apparatus as set forth in claim 13 wherein said single denture gripping projection is disposed generally between said pair of projections and lies in a plane generally perpendicular to a plane intersecting said pair of denture gripping projections.

15. The apparatus as set forth in claim 9 wherein one of said clamp means comprises a pair of laterally spaced denture gripping projections for gripping laterally spaced portions of said denture, the other of said clamp means comprises a single denture gripping projection for engaging a portion of said denture interjacent said laterally spaced portions of said denture.

16. The apparatus as set forth in claim 15 wherein said mount means includes a pair of generally parallel guides slidably mounting a longitudinally movable slide, one of said single denture gripping projection and said pair of projections being mounted on said slide.

17. The apparatus as set forth in claim 9 wherein said mount means comprises a pair of laterally spaced spherical bearing means and means for individually clamping said bearing means in adjusted positions.

18. Denture mounting apparatus comprising:
a longitudinally extending frame including movable clamping frame portions;
first and second, longitudinally spaced, denture support members for realeasably supporting first and second dentures;
means mounting each denture support member on said clamping frame portions for bodily movement toward and away from the other support member and for swinging movement relative to said frame portions to precisely align and orient said dentures; and
means for clamping said clamping frame portions to said denture support members in any selected one of a plurality of positions;
said clamping frame portions comprising first and second sets of laterally spaced, longitudinally extending, opposed clamping bars movable toward and away from each other;
said mounting means on each denture support member including a pair of laterally spaced mounting portions received between said opposed clamping bars;
said mounting means including means mounting said denture support members on said mounting portions for movement therewith when said bars are not clamped to said mounting portions and for swinging movement relative thereto when said bars are clamped to said mounting portions.

19. The mounting apparatus as set forth in claim 18 wherein said mounting means comprises universal joint mounting means; said frame portions including adjustable mounting members which in one position of adjustment permits each of said universal joint means to move toward the other universal joint means and in another position of adjustment prevent such movement.

20. Denture mounting apparatus comprising:
a longitudinally extending frame including movable clamping frame portions;
first and second, longitudinally spaced, denture support members for releasably supporting first and second dentures;
means mounting each denture support members on said clamping frame portions for bodily movement toward and away from the other support member and for swinging movement relative to said frame portions to precisely align and orient said dentures; and
means for clamping said clamping frame portions to said denture support members in any selected one of a plurality of positions;
said frame portions comprising generally horizontal, laterally spaced, vertically opposed clamping bars selectively movable toward and away from each other to clamp said denture support members in adjusted positions; said mounting means mounting said denture support members on said clamping bars for swinging movement between generally vertical positions perpendicular to said bars and generally horizontal positions parallel to said bars.

* * * * *